United States Patent

Laffan

Patent Number: 5,313,007
Date of Patent: May 17, 1994

[54] SUBSTITUTED PENTAALKYLCHROMANS

[75] Inventor: David Laffan, Visp, Switzerland

[73] Assignees: Lonza Ltd., Gampel/Valais, Switzerland; Sankyo Company Ltd., Tokyo, Japan

[21] Appl. No.: 26,811

[22] Filed: Mar. 5, 1993

Related U.S. Application Data

[62] Division of Ser. No. 977,255, Nov. 16, 1992, abandoned.

[30] Foreign Application Priority Data

Nov. 20, 1991 [CH] Switzerland ............... 3393

[51] Int. Cl.$^5$ .............................. C07C 39/19
[52] U.S. Cl. ..................................... 568/765
[58] Field of Search ........................ 568/765

[56] References Cited

U.S. PATENT DOCUMENTS 5,135,945 8/1992 Robinson et al. .............. 514/456

FOREIGN PATENT DOCUMENTS 0369874 5/1990 European Pat. Off. .
2364165 6/1974 Fed. Rep. of Germany .
3010504 10/1981 Fed. Rep. of Germany .

OTHER PUBLICATIONS

J. Med. Chem., 32, (1989), pp. 421 to 428.

Primary Examiner—Marianne M. Cintins
Assistant Examiner—John Peabody
Attorney, Agent, or Firm—Fisher, Christen & Sabol

[57] ABSTRACT

The substituted pentaalkylchromans of the general formula:

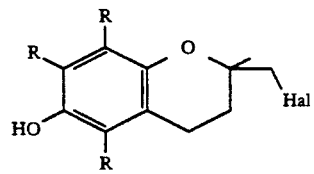

wherein R denotes a lower alkyl group having 1 to 4 C atoms and Hal denotes chlorine, bromine or iodine, are novel intermediates for the preparation of hypolipidaemic pharmaceuticals. A process for their preparation is described in which a trialkylhydroquinone is reacted with a halogenated butenol to give a substituted tetraalkylhydroquinone, which is finally cyclized to the final product.

2 Claims, No Drawings

SUBSTITUTED PENTAALKYLCHROMANS

This is a division of Ser. No. 07/977,255, filed on Nov. 16, 1992, now abandoned.

BACKGROUND OF THE INVENTION

1. Field of the Invention

The invention relates to substituted pentaalkylchromans of the general formula:

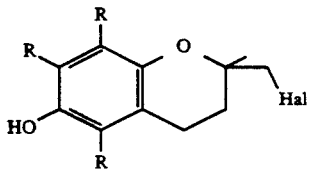

wherein R denotes a lower alkyl group having 1 to 4 C atoms and Hal denotes chlorine, bromine or iodine, and to a process for their preparation.

Pentaalkylchromans, in particular the tetramethyl derivatives of the general formula I, are useful intermediates for the preparation of, for example, hypolipidaemic pharmaceuticals [J. Med. Chem., 32, (1989), pp. 421 to 428].

2. Background Art

To prepare the hypolipidaemic pharmaceuticals, it was known to employ hydroxyalkylchromans of the general formula:

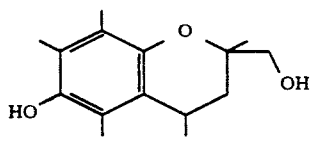

as intermediates [J. Med. Chem., 32, (1989), p. 421].

According to German Offenlegungsschrift 3,010,504, these hydroxyalkylchromans are obtainable from the corresponding hydroquinone and the corresponding butenediol with only a yield of 10 percent.

According to German Offenlegungsschrift 2,364,165, it is also known to prepare the hydroxyalkylchromans in a multi-step synthesis. However, this synthesis is very costly and not suitable for the industrial reaction.

BROAD DESCRIPTION OF THE INVENTION

The main objective is to provide a new path to the hypolipidaemic pharmaceuticals, which does not have the disadvantages of the known processes and intermediates. Other objectives and advantages of the invention are set out herein or are obvious herefrom to one skilled in the art.

The main object of the invention is achieved by the substituted pentaalkylchromans of the general formula I and using a simple process for their preparation. The objectives and advantages of the invention are achieved by the process and intermediates of the invention.

The invention involves a process for the preparation of substituted pentaalkylchromans of the general formula:

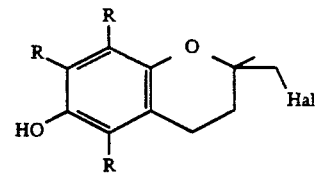

wherein R denotes a lower alkyl group having 1 to 4 C atoms and Hal denotes chlorine, bromine or iodine. In the first step, according to the invention process, a trialkylhydroquinone of the general formula:

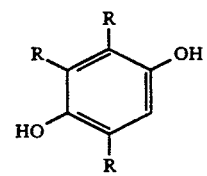

wherein R has the above-stated meaning is reacted with halogenated butenols of the formula:

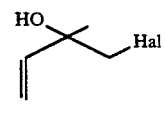

or

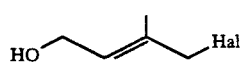

wherein Hal has the above-stated meaning, in the presence of a Lewis acid in such a way that, as an intermediate, a tetraalkylhydroquinine of the general formula:

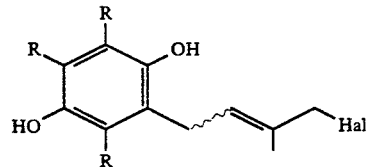

wherein R and Hal have the above-stated meanings, results. These compounds have not been described until now and are likewise part of the invention. The tetraalkylhydroquinone of the general formula IV is cyclized to the final product (of the general formula I) in the presence of a strong acid.

The invention also includes the substituted pentaalkylchromans of the general formula:

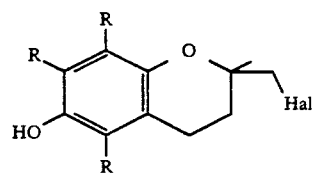

wherein R denotes a lower alkyl group having 1 to 4 C atoms and Hal denotes chlorine, bromine or iodine. Preferably the substituted pentaalkylchromans of the formula I is 2-chloromethyl-6-hydroxy-2,5,7,8-tetramethylchroman of the formula:

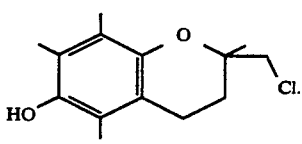

Ia

The invention also includes the substitutes tetraalkylhydroquinones of the general formula:

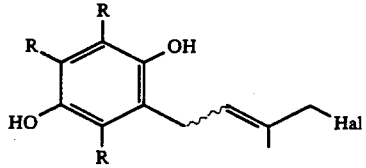

IV wherein R denotes a lower alkyl group having 1 to 4 C atoms and Hal denotes chlorine, bromine or iodine. Preferably the substituted tetraalkylhydroquinones of the general formula IV is 2-(1-chloro-2-methylbut-2-en-4-yl)-1,4-dihydroxy-3,5,6-trimethylbenzene of the formula:

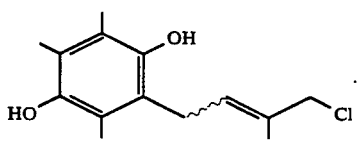

IVa

DETAILED DESCRIPTION OF THE INVENTION

Preferably, trimethylhydroquinone (formula II where R is CH₃) is reacted with 1-chloro-2-methylbut-3-en-2-ol (formula IIIa where Hal is Cl) to give the corresponding tetraalkylhydroquinone (formula IV where R is CH₃ and Hal is Cl).

The Lewis acid expediently employed is iron chloride, tin trifluoromethanesulfonate or boron trifluoride or one of its complex compounds, preferably boron trifluoride or one of its complex compounds, such as, boron trifluoride etherate. The Lewis acid is expediently employed in an amount from 1 mol to 5 mol, relative to the trialkylhydroquinone employed. The reaction is advantageously carried out in the presence of an inert solvent, such as, toluene or halogenated hydrocarbons, such as, methylene chloride, at a temperature between −10° and 50° C., preferably at room temperature.

Preferably, a process is used in which, when starting material (trialkylhydroquinone) is virtually no longer detectable in the reaction mixture, the reaction is immediately stopped and the resultant tetraalkylhydroquinone is isolated.

In the subsequent step, the tetraalkylhydroquinone of the general formula IV is cyclized in the presence of a strong acid to the final product of the general formula I.

The strong acid used is expediently a strong Brönsted acid, such as, trifluoromethanesulfonic acid, hydrochloric acid or fluorosulfonic acid. These Brönsted acids are expediently employed in an amount from 0.05 mol to 2 mol, relative to the tetraalkylhydroquinone.

The cyclization is advantageously carried out in the presence of a non-polar solvent, such as, toluene, carbon tetrachloride or hexane, at a temperature between −10° and 70° C., preferably at room temperature.

The resultant substituted pentaalkylchromans of the general formula I have not been described until now. The preferred derivative is 2-chloromethyl-6-hydroxy-2,5,7,8-tetramethylchroman where R is CH₃ and Hal is Cl.

EXAMPLE (a) Process for the preparation of 2-(1-chloro-2-methylbut-2-en-4-yl)-1,4-dihydroxy-3,5,6-trimethylbenzene Trimethylhydroquinone (2.00 g, 14 mmol) was suspended at room temperature in a mixture of chlorobenzene (10 ml) and hexane (5 ml). Boron trifluoride diethyl ether complex (3.60 ml of a 48 percent strength solution of boron trifluoride in diethyl ether, 1.95 g of boron trifluoride, 28 mmol) was then added in the course of 15 min. 1-Chloro-2-methylbut-3-en-2-ol 92.42 g, 20 mmol) was then added dropwise in the course of 15 min. After 30 min., the reaction mixture was filtered, and the filtrate was washed with chlorobenzene (10 ml) and dried at 40° C./20 mbar for 8 hours. 2.24 g (62.6 percent) of 2-(1-chloro-2-methylbut-2-en-4-yl)-1,4-dihydroxy-3,5,6-trimethylbenzene were obtained. The melting point of the product was 118° to 122° C. (decomposition). Other data regarding the product was:

¹H—NMR: (CDCl₃, 300 MHz) δ in ppm: 5.50 (t, 1H, J=7.5 Hz); 4.02 (s, 2H); 3.45 (d, 2H, J=7.5 Hz); 2.17 (s, 6H); 2.15 (s, 3H); 1.95 (s, 3H).

Isomer: 5.48 (t, 1H, J=7.5 Hz); 4.02 (s, 2H); 3.48 (d, 2H, J=7.5 Hz); 2.17 (s, 6H); 2.15 (s, 3H); 1.95 (s, 3H).

(b) Process for the preparation of 2-chloromethyl-6-hydroxy-2,5,7,8-tetramethylchroman 2-(1-Chloro-2-methylbut-2-en-4-yl)-1,4-dihydroxy-3,5,6-trimethylbenzene (4.2 g, 16 mol) was suspended in carbon tetrachloride (200 ml). Trifluoromethanesulfonic acid (1.44 ml, 2.44 g, 16 mmol) was then added and the reaction mixture was stirred. After 30 min., water (100 ml) was added and the mixture was extracted with methylene chloride (100 ml). The organic phase was dried (MgSO₄) and concentrated. This gave crude 2-chloromethyl-6-hydroxy-2,5,7,8-tetramethylchroman (5.3 g). Recrystallization from hexane (40 ml) gave 2.7 g (64 percent) of pure 2-chloromethyl-6-hydroxy-2,5,7,8-tetramethylchroman. The melting point of the product was 77° to 82° C. Other data regarding the product was:

¹H—NMR: (CDCl₃, 300 MHz), δ in ppm: 4.25 (s, 1H); 3.53 (d, 1H, J=12.0 Hz); 3.50 (d, 1H, J=12.0 Hz); 2.62 (t, 2H, J=7.0 Hz); 2.17 (s, 3H); 2.11 (s, 6H); 2.10–2.02 (m, 1H); 1.90–1.78 (m, 1H); 1.40 (s, 3H).

What is claimed is:

1. A substituted tetraalkylhydroquinone of the formula:

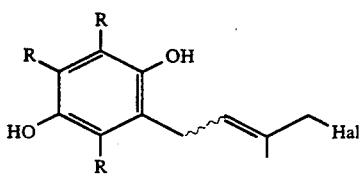

IV wherein R denotes a lower alkyl group having 1 to 4 C atoms and Hal denotes chlorine, bromine or iodine.
2. 2-(1-Chloro-2-methylbut-2-en-4-yl)-1,4-dihydroxy-3,5,6-trimethylbenzene of the formula:
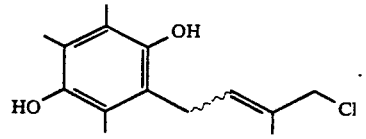
IVa
* * * * *